United States Patent [19]
Solomon et al.

[11] Patent Number: 5,858,732
[45] Date of Patent: Jan. 12, 1999

[54] WIDE DYNAMIC RANGE NUCLEIC ACID DETECTION USING AN AGGREGATE PRIMER SERIES

[75] Inventors: Natalie A. Solomon, Buffalo Grove; Stanley R. Bouma, Grayslake, both of Ill.

[73] Assignee: Abbott Laboratories, Abbott Park, Ill.

[21] Appl. No.: 697,404

[22] Filed: Aug. 23, 1996

Related U.S. Application Data

[63] Continuation of Ser. No. 444,615, May 19, 1995, abandoned.

[51] Int. Cl.$^6$ .............................. C12P 19/34; C12Q 1/68; C07H 21/02; C07H 21/04
[52] U.S. Cl. .................................. 435/91.2; 435/6; 435/5; 435/91.1; 536/24.3; 536/24.31; 536/24.33
[58] Field of Search .................................. 435/5, 6, 91.1, 435/91.2; 536/24.3, 24.31, 24.33, 23.1

[56] References Cited

U.S. PATENT DOCUMENTS

| | | | |
|---|---|---|---|
| 5,213,961 | 5/1993 | Bunn et al. | 435/6 |
| 5,219,727 | 6/1993 | Wang et al. | 435/6 |
| 5,389,512 | 2/1995 | Sninsky et al. | 435/5 |

FOREIGN PATENT DOCUMENTS

| | | |
|---|---|---|
| PCT 0 320 308 | 12/1988 | European Pat. Off. . |
| PCT 0 357 011 | 8/1989 | European Pat. Off. . |
| WO 93/23573 | 5/1993 | WIPO . |

OTHER PUBLICATIONS

Quantification of Hepatitis B Virus DNA by Competitive Amplification and Hybridization on Microplates jalava, et al *Biotechniques,* vol. 15, No. 1, pp. 134–139, 1993.

Kinetic PCR Analysis: Real–time Monitoring of DNA Amplification Reactions Higuchi, et al *Bio/Technology,* vol. 11, pp. 1026–1030, 1993.

Quantification of Gene Expression over a Wide Range by the Polymerase Chain Reaction Kinoshita, et al *Analytical Biochemistry,* vol. 206, pp. 231–235, 1992.

Quantitation of Plasma Human Immunodeficiency Virus Type 1 RNA by Competitive Polymerase Chain Reaction Scadden, et al *Journal of Infectious Diseases,* vol. 165, pp. 1119–1123, 1992.

Okamoto et al, (1993), "Detection of Hepatitis C virus genome in human serum by multi–targeted polymerase chain reaction", J. Med. Virol. 41:6–10.

Matthews et al, (1988), "Analytical strategies for the use of DNA probes", Anal. Biochem. 169:1–25.

He et al, (Jul. 1994), "Primers are decisive for sensitivity of PCR", Biotechniques 17(1):82, 84, 86, 87.

Sugimoto et al, (1993), "Quantitative detection of DNA by coamplification polymerase chain reaction: A wide detectable range controlled by the thermodynamic stability of primer template duplexes", Anal. Biochem. 211:170–172.

Becker–Andre et al, (1989), "Absolute mRNA quantification using the polymerase chain reaction (PCR). A novel approach by a PCR aided transcript titration assay (PATTY)", Nucleic Acids Res. 17(22):9437–9446.

Dostal et al, (1994), "An improved method for absolute quantification of mRNA using multiplex polymerase chain reaction: determination of renin and angiotensis mRNA levels in various tissues", Anal. Biochem. 223:239–250.

Celi et al, (1994), "Determination of gene dosage by a quantitative adaption of the polymerase chain reaction (gd–PCR): Rapid detection of deletions and duplications of gene sequences", Genomics 21:304–310.

Wong et al, (1994), "Monitoring mRNA expression by polymerase chain reaction: The primer dropping method", Anal. Biochem. 223:251–258.

Foley et al, (1993), "Quantitation of RNA using the polymerase chain reaction", Trends Genet. 9(11):380–385.

Apostolakos et al, (1993), "Measurement of gene expression by multiplex competitive polymerase chain reaction", Anal. Biochem. 213:277–284.

Chelly et al, (1988), "Transcription of the dystrophin gene in human muscle and non–muscle tissues", Nature 333:858–860.

Rappolee et al, (1988), "Wound macrophages express TGF–a and other growth factors in vivo: analysis by mRNA phenotyping", Science 241:708–712.

Hetu et al, "A non–isotopic nested polymerase chain reaction method to quantitate minimal residual disease in patients with non–Hodgkin's lymphoma", Mol. Cell. Biol. 8:449–457, Dec. 1994.

*Primary Examiner*—Jeffrey Fredman
*Attorney, Agent, or Firm*—Paul D. Yasger

[57] ABSTRACT

The present invention provides a method of detecting the amount of a target sequence which may be present in a test sample. The method uses an aggregate primer series, which comprises at least two primer sets, in an amplification reaction to detect the relative concentration of a target sequence which may be present in a test sample. The primer sets have different sensitivities and hybridize with sub-target sequences which are different regions of the target sequence. The method generally comprises cycling a test sample suspected of containing a target sequence, an aggregate primer series, and means necessary for performing an amplification reaction; and detecting any amplified sub-target sequences. Based on a qualitative detection of the amplified sub-target sequences generated by individual primer sets, the relative quantity of the target sequence can be determined.

13 Claims, 3 Drawing Sheets

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 37 base pairs
        ( B ) TYPE: nucleic acid
        ( C ) STRANDEDNESS: double
        ( D ) TOPOLOGY: linear     ( i i ) MOLECULE TYPE: genomic DNA     ( x i ) SEQUENCE DESCRIPTION: SEQ ID NO:1:

GGGCAAGGTG AACGTGGATG AAGTTGGTGG TGAGGCC        37

( 2 ) INFORMATION FOR SEQ ID NO:2:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear     ( i i ) MOLECULE TYPE: genomic DNA (HIV)

( x i ) SEQUENCE DESCRIPTION: SEQ ID NO:2:

GGCAAGGCCA ATGGACATAT CAAATTTATC AAGAGCCATT TAAAAATC        48

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: synthetic DNA     ( i x ) FEATURE:
        ( A ) NAME/KEY: 5'biotin
        ( B ) LOCATION: 1

( x i ) SEQUENCE DESCRIPTION: SEQ ID NO:3:

GGGCAAGGTG AACGTGGA        18

( 2 ) INFORMATION FOR SEQ ID NO: 4:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear     ( i i ) MOLECULE TYPE: synthetic DNA     ( i x ) FEATURE:
        ( A ) NAME/KEY: 5'phosphate
        ( B ) LOCATION: 1

( i x ) FEATURE:
        ( A ) NAME/KEY: 3'biotin
        ( B ) LOCATION: 17

( x i ) SEQUENCE DESCRIPTION: SEQ ID NO: 4:

CCACGTTCAC CTTGCCC       17

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: synthetic DNA     ( i x ) FEATURE:
        ( A ) NAME/KEY: 5'phosphate
        ( B ) LOCATION: 1

( x i ) SEQUENCE DESCRIPTION: SEQ ID NO:5:

GAAGTTGGTG GTGAGGCC       18

( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( i i ) MOLECULE TYPE: synthetic DNA     ( i x ) FEATURE:
        ( A ) NAME/KEY: 5'adamantane
        ( B ) LOCATION: 1

( x i ) SEQUENCE DESCRIPTION: SEQ ID NO:6:

GGCCTCACCA CCAACTTCA       19

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: synthetic DNA     ( i x ) FEATURE:
        ( A ) NAME/KEY: 5'fluorescein
        ( B ) LOCATION: 1

( x i ) SEQUENCE DESCRIPTION: SEQ ID NO:7:

GGCAAGGCCA ATGGACATAT CAAA       24

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: synthetic DNA     ( i x ) FEATURE:
        ( A ) NAME/KEY: 5'phosphate
        ( B ) LOCATION: 1

( i x ) FEATURE:
        ( A ) NAME/KEY: 3'fluorescein
        ( B ) LOCATION: 21

( x i ) SEQUENCE DESCRIPTION: SEQ ID NO:8:

GATATGTCCA TTGGCCTTGC C        21

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: synthetic DNA     ( i x ) FEATURE:
        ( A ) NAME/KEY: 5'phosphate
        ( B ) LOCATION: 1

( i x ) FEATURE:
        ( A ) NAME/KEY: 3'biotin
        ( B ) LOCATION: 21

( x i ) SEQUENCE DESCRIPTION: SEQ ID NO:9:

ATCAAGAGCC ATTTAAAAAT C        21

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: synthetic DNA     ( i x ) FEATURE:
        ( A ) NAME/KEY: 5'biotin
        ( B ) LOCATION: 1

( x i ) SEQUENCE DESCRIPTION: SEQ ID NO:10:

GATTTTTAAA TGGCTCTTGA TAAA        24

( 2 ) INFORMATION FOR SEQ ID NO:11:

( i ) SEQUENCE CHARACTERISTICS:
        ( A ) LENGTH: 477 base pairs
        ( B ) TYPE: nucleic acid
        ( C ) STRANDEDNESS: double
        ( D ) TOPOLOGY: linear     ( i i ) MOLECULE TYPE: genomic DNA (HBV)

( x i ) SEQUENCE DESCRIPTION: SEQ ID NO:11:

ATACCACAGA GTCTAGACTC GTGGTGGACT TCTCTCAATT TTCTAGGGGG        50

| | | | | |
|---|---|---|---|---|
| AACACCCGTG | TGTCTTGGCC | AAAATTCGCA | GTCCCAAATC | TCCAGTCACT | 100
| CACCAACCTG | TTGTCCTCCA | ATTTGTCCTG | GTTATCGCTG | GATGTGTCTG | 150
| CGGCGTTTTA | TCATCTTCCT | CTGCATCCTG | CTGCTATGCC | TCATCTTCTT | 200
| GTTGGTTCTT | CTGGACTATC | AAGGTATGTT | GCCCGTTTGT | CCTCTAATTC | 250
| CAGGATCATC | AACAACCAGC | ACCGGACCAT | GCAAAACCTG | CACAACTCCT | 300
| GCTCAAGGAA | CCTCTATGTT | TCCCTCATGT | TGCTGTACAA | AACCTACGGA | 350
| TGGAAACTGC | ACCTGTATTC | CCATCCCATC | ATCTTGGGCT | TTCGCAAAAT | 400
| ACCTATGGGA | GTGGGCCTCA | GTCCGTTTCT | CTTGGCTCAG | TTTACTAGTG | 450
| CCATTTGTTC | AGTGGTTCGT | AGGGCTT | | | 477

(2) INFORMATION FOR SEQ ID NO:12:

(i) SEQUENCE CHARACTERISTICS:
        (A) LENGTH: 72 base pairs
        (B) TYPE: nucleic acid
        (C) STRANDEDNESS: double
        (D) TOPOLOGY: linear     (ii) MOLECULE TYPE: genomic DNA (HBV)

(xi) SEQUENCE DESCRIPTION: SEQ ID NO:12:

| | | | | |
|---|---|---|---|---|
| TTCAAGCCTC | CAAGCTGTGC | CTTGGGTGGC | TTTGGGGCAT | GGACATTGAC | 50
| CCGTATAAAG | AATTTGGAGC | TT | | | 72

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear     (ii) MOLECULE TYPE: synthetic DNA     (xi) SEQUENCE DESCRIPTION: SEQ ID NO:13:

| | | | |
|---|---|---|---|
| ATACCACAGA | GTCTAGACTC | GTGGTGGACT | 30

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear     (ii) MOLECULE TYPE: synthetic DNA     (xi) SEQUENCE DESCRIPTION: SEQ ID NO:14:

| | | | |
|---|---|---|---|
| AAGCCCTACG | AACCACTGAA | CAAATGGCAC | 30

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear     (ii) MOLECULE TYPE: synthetic DNA     (xi) SEQUENCE DESCRIPTION: SEQ ID NO:15:

| | | |
|---|---|---|
| TTCAAGCCTC | CAAGCTGTGC | CTTGG | 25

( 2 ) INFORMATION FOR SEQ ID NO:16:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear     ( i i ) MOLECULE TYPE: synthetic DNA     ( x i ) SEQUENCE DESCRIPTION: SEQ ID NO:16:

AAGCTCCAAA TTCTTTATAC GGGTCAATG                              2 9

WIDE DYNAMIC RANGE NUCLEIC ACID DETECTION USING AN AGGREGATE PRIMER SERIES

This application is a continuation of U.S. patent application Ser. 08/444,651, filed may 19, 1995, now abandoned.

FIELD OF THE INVENTION

The present invention relates to methods for amplifying and detecting a nucleic acid sequence which may be present in a test sample and in particular, to methods for quantitatively detecting a nucleic acid sequence which may be present in a test sample.

BACKGROUND OF THE INVENTION

Methods for amplifying a target nucleic acid sequence that may be present in a test sample are, by now, well known in the art. Such methods include the polymerase chain reaction (PCR) which has been described in U.S. Pat. Nos. 4,683,195 and 4,683,202, the ligase chain reaction (LCR) described in EP-A-320 308, gap LCR (GLCR) described in European Patent Application EP-A-439 182, multiplex LCR described in International Patent Application No. WO 93/20227 and the like. These methods have found widespread application in the medical diagnostic field as well as the fields of genetics, molecular biology and biochemistry. Unfortunately, one drawback of nucleic acid amplification reactions is that they are mostly qualitative.

The nature of amplification reactions makes it difficult for them to be used to quantitatively detect the presence of a target sequence which may be present in a test sample. Accordingly, while traditional amplification reactions are useful for detecting the presence of a minute quantity of a target sequence in a test sample, traditional amplification reactions generally cannot be employed to determine the quantity of a target sequence in a test sample. However, variations of traditional amplification reactions have been developed which enable quantitative amplification reaction analysis.

One quantitative amplification reaction is called "competitive amplification." This method is commonly applied to PCR. According to competitive amplification reactions, a standard nucleic acid sequence competes with a target sequence during the amplification reaction. Generally, the standard sequence and a sample suspected of containing a target sequence are combined in a dilution series in which the amount of the standard sequence is constant in all members of the series. Alternatively, the standard sequence and sample sequence are combined in a dilution series in which the amount of standard sequence is varied among the members of the dilution series. In any case, the concentration of the standard sequence in the members of the dilution series, is known. PCR is then performed on all members of the dilution series and results in the production of a mixture of two nucleic acid sequence species. One species derived from the standard sequence and one species derived from the sample sequence. The concentration of each species in a particular dilution depends on the number of copies of the standard and sample sequences in the dilution prior to amplification. During the amplification reaction, detectable groups are typically introduced into both types of sequences. After amplification, the two species are separated and the amount of detectable group incorporated into each species is determined. This detection procedure is performed for each member of the dilution series. A competition curve can then be generated and the amount of sample sequence can be extrapolated based on the known amounts of standard sequence.

Methods of competitive amplification have been described in U.S. Pat. No. 5,219,727; Kinoshita T., et. al., *Analytical Biochemistry* 206: 231–235 (1992); and Jalava T., et. al., *BioTechniques*15:(1), 134–205 (1993). While these competitive amplification techniques have shown utility, they require substantial amounts of sample preparation as well as technician interaction and a concomitant risk of sample contamination. In addition, the use of a standard sequence adds an additional reagent not generally a requirement of traditional amplification reactions. Moreover, performing amplification on members of a dilution series requires more reagents than performing amplification on a single sample. All of these factors add to the costs of performing competitive amplification reactions.

Another quantitative amplification reaction is "kinetic amplification analysis". This method takes advantage of a dye's ability to bind double stranded nucleic acid sequences. For example, PCR generally produces double stranded nucleic acid sequences. In the presence of a dye, such as ethidium bromide, which binds double stranded nucleic acid sequences, an increase in fluorescence is observed with successive rounds of PCR amplification. The greater the amount of target nucleic acid sequence in a test sample, the earlier a rise in fluorescence will be observed.

Kinetic amplification analysis has been described in Higuchi R., et. al., *Bio/Technology* 11: 1026–1030 (1993). Unfortunately, the efficiency of an amplification reaction can vary from sample to sample. Hence, while two samples may contain equivalent target sequence concentrations, different fluorescent rates for the two samples may be obtained in a kinetic amplification analysis. Accordingly, this method is not always useful in a clinical setting because of the wide variety of samples which are assayed.

Thus there is a need for a method of quantitatively performing an amplification reaction which does not require excess technician manipulation or reagents, and can be employed in a clinical laboratory setting.

SUMMARY OF THE INVENTION

The instant invention provides a method of detecting the relative or approximate amount of a target sequence in a test sample which does not require the preparation of a dilution series, and therefore, does not require large amounts of reagents and technician interaction. Generally, the method comprises contacting a test sample suspected of containing a target nucleic acid sequence with a nucleic acid amplification reaction mixture comprising a first primer set capable of hybridizing with a first sub-target region of the target nucleic acid sequence, and a second primer set capable of hybridizing with a second sub-target region of the target nucleic acid sequence. The first and second sub-target regions of the target sequence are different; and the first and second primer sets are selected such that the first primer set is capable of producing a detectable amplicon essentially only at or above a first threshold concentration of the target sequence, and the second primer set is capable of producing a detectable amplicon essentially only at or above a second threshold concentration of the target nucleic acid sequence. Threshold concentrations at which the primer sets are capable of producing a detectable amplicon are also different from one another.

After the target sequence and reaction mixture are contacted, the resulting mixture is subjected to amplification conditions sufficient to produce a detectable amplicon from at least one of the primer sets when the test sample contains a concentration of target nucleic acid sequence which is at or above the threshold concentration at which the primer set is capable of producing a detectable amplicon. An amplicon, if produced, from at least one primer set is then detected in the reaction mixture so as to determine whether the test sample contained a concentration of target nucleic acid sequence essentially at or above the threshold concentration corresponding to that primer set.

The primer sets can be employed with various amplification reaction protocols, but they are preferably employed according to LCR or PCR protocols. Additionally, members of the individual primer sets can carry a label to facilitate detection of any sub-target sequence copies which may be produced.

DETAILED DESCRIPTION OF THE INVENTION

The present method does not require substantial sample manipulation or preparation. For example, the method does not require the production of a dilution series. Nor does the method require the performance of multiple amplification reactions to determine the relative quantity of a target sequence which may be present in a test sample. Accordingly, the method can be run in a single vessel which therefore alleviates contamination problems associated with excessive sample manipulation. Additionally, less reagents are required to perform the instant method. For these and other reasons which will become apparent, the method herein provided is readily amenable to automated operation.

The method herein provided is applicable to nucleic acid amplification reactions (hereinafter "amplification reactions") which employ primer sets (variably referred to as "probe sets") to amplify a target nucleic acid sequence. Briefly, the method uses an "aggregate primer series", which comprises at least two primer sets, in an amplification reaction to detect the relative concentration of a target sequence which may be present in a test sample. The method generally comprises contacting a test sample suspected of containing a target sequence with a nucleic acid amplification reaction mixture comprising an aggregate primer series, and other reagents suitable for performing an amplification reaction. The reaction mixture can then be subjected to amplification conditions to allow members of the aggregate primer series to hybridize with and amplify any "sub-target sequences" which are regions of the target sequence. The presence of any amplified sub-target sequences can then be detected. Collectively, the amplified sub-target sequences generated by an individual primer set will be referred to as an "amplicon". Based on a qualitative detection of the amplicons generated by individual primer sets which comprise the aggregate primer series, the approximate quantity of the target sequence can be determined. Specifically, because an individual primer set, as used herein, yields a detectable amplicon in the presence of a "threshold concentration" of the target sequence, a detectable signal from an individual primer set indicates there is at least as much target sequence in the test sample as that primer set's threshold concentration. On the other hand, if no detectable amplicon is produced by an individual primer set, it can be determined that the target sequence is not present at a concentration that is essentially at or above that primer set's threshold concentration.

The method will now be explained in further detail. A test sample is typically anything suspected of containing a target sequence. Test samples can be prepared using methodologies well known in the art such as by taking a specimen from a patient and, if necessary, disrupting any cells contained therein to release nucleic acids. It will be understood that the individual primer sets comprising an aggregate primer series can be contacted with a test sample that is contained in several individual vessels. Preferably, however, the aggregate primer series is contacted with a test sample that is contained in a single vessel.

A target sequence is generally a nucleic acid sequence (e.g. RNA or DNA) comprising at least two sub-target sequences to which members of the aggregate primer series hybridize. Sub-target sequences are characteristic subsets of the target sequence in the sense that sub-target sequences are characteristically found in a gene or organism the relative amount of which can be determined according to the present invention. Typically, the sub-target sequence is present in the target sequence in a consistent copy number, preferably, the sub-target sequence is present in the target sequence in a 1-to-1 ratio. Thus, a target sequence may comprise any sequence suspected of comprising characteristic sub-target sequences or regions.

The target sequence can be single stranded, double stranded, continuous, or fragmented so long as portions of it are sufficiently continuous for the individual primer sets to hybridize and amplify any sub-target sequences which can be, for example, a gene, a gene fragment or an extra chromosomal nucleic acid sequence. While the sequence of the entire target sequence may not be known, it is generally the case that at least a portion of the sub-target sequences is known. For example, in the case where PCR is employed, the ends of the sub-target sequences are known, and in cases where LCR is employed, the entire sub-target sequence is known.

The present method finds particular utility in determining the approximate quantity of a target sequence typically having at least 1 Kb such as, for example, a bacterial or viral genome. For example, the target sequence may comprise the genome of an organism such as *Chlamydia trachomatis* where the sub-target sequences could comprise regions of the MOMP gene, the LPS gene and/or the cryptic plasmid. Alternatively, all sub-target sequences might be found within any one of the three mentioned regions. Additionally, a viral genome could comprise a target sequence and the sub-target sequences could comprise sequences that are characteristically present in that viral genome. For example, sub-target sequences of the HIV genome could comprise regions of the gene coding for the P24 antigen and the pol gene. Similarly to above, all sub-target sequences might alternatively be found in either the gene coding for the P24 antigen or the pol gene.

An aggregate primer series comprises at least two primer sets which are specific for distinct sub-target sequences. Additionally, the sensitivities of the individual primer sets are typically known and the sensitivities of at least two of the individual primer sets are different or distinguishable from each other. When a solution comprising an aggregate primer series, a target sequence as well as other reagents suitable for performing an amplification reaction are placed under amplification conditions, the primer sets amplify their respective sub-target sequences. Because the respective sub-target sequences are characteristic subsets of the target sequence, the sensitivities of the individual primer sets are ultimately dependent upon the target sequence's concentration. A target sequence concentration at which an individual primer set begins producing a detectable amplicon is referred to as that primer set's threshold concentration. In the presence of its threshold concentration, a primer set will generate an amplicon in a quantity that can be detected. On the other hand, in the absence of its threshold concentration, the quantity of amplicon produced by an individual primer set cannot be detected. In this manner, a primer set's production, or non-production, of a detectable amplicon can be correlated to the amount of target sequence in the test sample, and by using two or more primer sets with different threshold concentrations, a semiquantitative detection method is achieved.

The sensitivities, or threshold concentrations, of at least two primer sets can readily be determined by running an amplification reaction with the primer sets in the presence of a given concentration of the target sequence. The amplicons, if any, can then be detected to determine if the target sequence concentration was great enough to enable the production of a detectable amplicon. For example, a "primer set A" and a "primer set B" can be contacted with a test sample containing 10,000 molecules of a target sequence comprising sub-target sequences for which primer set A and primer set B are specific. The resulting mixture can then be placed under amplification conditions and any amplicons can be detected. In the event primer A produced enough amplicon to be detected and primer set B did not, it could be determined that the sensitivities of the primer sets were distinguishable and that primer set A's threshold concentration had been met or was exceeded at 10,000 target molecules. Accordingly, at the primer concentrations employed, the sensitivities of these primer sets were "naturally" distinguishable. A more accurate threshold concentration for primer set A could be determined by repeating the amplification reaction with decreasing target concentrations. The threshold concentration for primer set B could be determined by running further amplification reactions with increasing concentrations of the target sequence. The target sequence concentration at which primer set B initially generates a detectable amplicon would be primer set B's threshold concentration. While it is preferable to determine the sensitivities of multiple primer sets by employing them in the same amplification reaction, it will be understood that the sensitivities of multiple primer sets can be determined individually by employing them in separate amplification reactions.

A sensitivity determined as above will be referred to as a primer set's "inherent sensitivity", and such a sensitivity generally is inherent to the conditions under which the sensitivity was determined. Thus, if the primer set was employed in an amplification reaction with a different number of amplification cycles, the sensitivity of the primer set may change. For example, if the number of amplification cycles was increased, the primer set's threshold concentration may decrease. Conversely, if the number of amplification cycles was decreased, the primer set's threshold concentration may increase. Those skilled in the art will appreciate that the sensitivity or threshold concentration of a primer set is not absolute and that minor deviations from the exact threshold concentration may be exhibited from amplification reaction to amplification reaction without departing from the spirit and scope of the present invention. Thus, it will be understood by those skilled in the art that a primer set will produce a detectable amplicon essentially only at or above its threshold concentration.

In some cases, it may be desirable to change a primer set's inherent sensitivity such as when the sensitivities of two or more primer sets comprising an aggregate primer series are not naturally distinguishable. In such cases, the sensitivity of one or more primer sets can be adjusted. Adjusting a primer set generally involves altering the sensitivity of a primer set such that it produces a detectable amplicon in the presence of a threshold concentration that is distinguishable from the threshold concentration of another primer set. Hence, an "imbalance" among the primer sets is created whereby the individual primer sets employed in an amplification reaction generate detectable amplicons at different threshold concentrations. Thus, when the sensitivities of two or more primer sets comprising an aggregate primer series are not naturally distinguishable, at least one of the individual primer sets is adjusted such that it produces a detectable amplicon in the presence of a threshold concentration that is different from the other primer set(s).

The method employed for adjusting individual primer sets is a matter of choice. A preferred method of adjusting the sensitivity of a primer set is through modulating the concentration of the primer set employed in an amplification reaction. It is impossible to predict precisely the concentration of a primer set at which it will produce a detectable amplicon in the presence of a selected threshold concentration. However, this determination can be readily determined empirically through simple experiments It has generally been the case that for a given number of amplification cycles, increasing the concentration of a primer set employed in an amplification reaction increases the primer set's sensitivity. For example, if after 25 amplification cycles a 10 nM concentration of a primer set is not producing a detectable amplicon at 10,000 copies of the target sequence, the sensitivity of that primer set generally can be increased by increasing its concentration in the amplification reaction. For instance, using a 100 nM concentration of that primer set may produce a detectable amplicon in the presence of 10,000 target sequences after 25 amplification cycles. Conversely, if after 25 amplification cycles a 10 nM concentration of a primer set is producing a detectable amplicon at 10,000 copies of the target sequence, the sensitivity of that primer set generally can be decreased by decreasing its concentration in the amplification reaction. For instance, 100,000 target sequences may be required to enable the production of a detectable amplicon using a 1 nM concentration of that primer set after 25 amplification cycles.

Using imperfectly complementary primers (variably referred to as "mismatched primers") could also be employed to adjust the sensitivity of a primer set. For example, if after a given number of amplification cycles a primer set will produce a detectable amplicon in the presence of 100 copies of a target sequence, the sensitivity of this primer set could be decreased by introducing into the primer set, nucleotides that don't match the sub-target sequence for which the primer set is specific. Thus, the adjusted primer set is not perfectly complementary to its target. Because the binding efficiency of such an adjusted primer for its target would be decreased, a greater number of target sequences may be required to produce a detectable amplicon after a given number of amplification cycles. Accordingly, the adjusted primer set may have a threshold concentration of 1,000 target sequences.

A target sequence may comprise multiple copies of a sub-target sequence. In such a case, the threshold concentration of an individual primer set which is specific for the multi-copy sequence may be lower than that expected for a primer set which is specific for a sub-target sequence which has a single copy within the target sequence. Of course, account for multiple copies of a sub-target sequence can be taken through the process of adjusting a primer set specific for such a sequence. For example, a primer set specific for a multiple copy sub-target sequence may be employed at a lower concentration to maintain its desired threshold concentration.

It will also be understood that the number of amplification cycles used in determining a primer set's threshold concentration, should be roughly equivalent to the number of amplification cycles employed in an amplification reaction which uses that primer set. Additionally, sensitivities of detection systems often show variability. Accordingly, the same detection system used to adjust primers, or to otherwise determine their sensitivities, should be employed to execute the method herein provided.

The number of primer sets comprising an aggregate primer series is largely a matter of choice for one skilled in the art which can be based upon the meaningful ranges in which a target sequence can be categorized. For example, if the number of virus particles in a sample can be used to indicate several different stages of a disease, more than two primer sets may be desired. Thus, if the number of meaningful ranges into which a target sequence could be categorized was n+1, n primer sets could be employed to cover such ranges. For example, 2, 3, 4, 5, 6, 7, 8, 9, or 10 primer sets could be employed according to the instant invention. In this manner the relative number of target sequences, in this case the viral genome, can be determined and correlated to various levels of the virus in the test sample. It will be understood by those skilled in the art that the present method provides an approximate value of the number of target sequences in a test sample. Specifically, the use of an aggregate primer supplies ranges of values into which the number of target sequences can be placed.

However, the more precisely the sensitivities of the primer sets can be adjusted, the narrower the numerical range will be for the relative concentration of the target sequence in the test sample. Thus, for example, if the sensitivities of two primer sets were adjusted so that one adjusted primer set had a threshold concentration of 1,000 or more target sequences and the other adjusted primer set had a threshold concentration of 10,000 or more target sequences, one could determine if less than 1,000 target sequences, between 1,000 and 10,000 target sequences, or more than 10,000 target sequences were present in the test sample. However, if the same pair of primer sets are adjusted to threshold concentrations of 10 and 100 target sequences, it could be determined if less than 10, between 10 and 100, or more than 100 target sequences were present in the test sample. Hence, "approximate" as used herein is intended to mean that the number of target sequences in a test sample is placed within a bracket of values but the values forming such bracket may be close enough to yield a definite number of target sequences.

An aggregate primer series can be employed in a single amplification reaction to determine the relative amount of a target sequence in a test sample. Amplification reactions such as, for example, LCR, GLCR and PCR are well known in the art. These reactions typically employ primers to repeatedly generate copies of a target nucleic acid sequence which is usually a small region of a much larger nucleic acid sequence. Primers and probes are themselves nucleic acid sequences that are complementary to regions of a target sequence and under amplification conditions, hybridize or bind to the complementary regions of the target sequence. Copies of the target sequence are typically generated by the process of primer extension and/or ligation which utilizes enzymes with polymerase or ligase activity, separately or in combination, to add nucleotides to the hybridized primers and/or ligate adjacent primer pairs. While enzymatic methods of polymerization and ligation are predominant, other methods such as, for example, chemical polymerization and ligation are equally suitable for use according to the present invention. The nucleotides that are added to the primers or probes, as monomers or preformed oligomers, are also complementary to the target sequence. Once the primers or probes have been sufficiently extended and/or ligated they are separated from the target sequence, for example, by heating the reaction mixture to a "melt temperature" which is one where complementary nucleic acid strands dissociate. Thus, a sequence complementary to the target sequence is formed.

A new amplification cycle can then take place to further amplify the number of target sequences by separating any double stranded sequences, allowing primers to hybridize to their respective targets, extending and/or ligating the hybridized primers and re-separating. The complementary sequences that are generated by amplification cycles can serve as templates for primer or probe extension to further amplify the number of target sequences. Hence, multiple copies of the target sequence and its complementary sequence are produced. Hence, under amplification conditions an aggregate primer series will amplify sub-target regions of the target sequence when it is present.

Generally, two primers which are complementary to a portion of a target strand and its complement are employed in PCR. For LCR, four primers, two of which are complementary to a target sequence and two of which are similarly complementary to the targets complement, are generally employed. In addition to the primer sets and enzymes previously mentioned, a nucleic acid amplification reaction mixture may also comprise other reagents which are well known and include but are not limited to: enzyme cofactors such as magnesium; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

In addition to the enzymatic thermal amplifications described above, isothermal enzymatic amplification reactions could also be employed according to the instant invention. For example, "3SR" (Self-Sustained Sequence Replication) described in Fahy, E., et. al., *PCR Methods and Applications*, 1: 25–33 (1991) and "SDA" (Strand Displacement Amplification) described in Walker, G. T., et. al., *PNAS* 89: 392–396 (1992) are amplification reactions which are similar to PCR, and with minor modifications, could be employed in the present method. Such modifications are detailed in the literature and are well known to those skilled in the art. For example, the use of avian myeloblastosis virus (AMV) reverse transcriptase (RT), *E. coli* RNase H and T7 RNA polymerase as well as ribonucleotide triphosphates (rNTPs) can be employed for 3SR in place of the enzyme and dNTPs employed in PCR. Similarly, *E. coli* DNA polymerase I (exo- Klenow polymerase) instead of, for example, Taq polymerase, and a restriction enzyme such as HincII plus deoxyadenosine 5'-[α-thio]triphosphate can be employed in SDA.

Amplification reactions, including but not limited to those exemplified above, can be employed in the present method. Preferably, a reaction mixture is cycled between about 15 and about 100 times, more preferably, between about 25 and about 60 times. It should also be noted that the concentrations of, for example, the nucleotide triphosphates, enzymes and cofactors employed in the instant method may be higher than those normally used in a typical amplification reaction.

After an aggregate primer series is employed in an amplification reaction, the amplicons produced, if any, can be detected. Because a plurality of amplicons can be produced, it may be desirable to spatially separate the amplicons. It will be understood that spatially separating amplicons is generally a matter of choice for one skilled in the art which is largely based upon the type of detection method employed.

In the event amplicon separation is desired, separation is only required to the extent that the amplicons can be differentiated from each other. Multiple amplicons can be spatially separated based on the position or location of a signal. Such spatial differentiation may be accomplished by size, molecular weight, charge density, magnetic properties, specific binding properties and the like. Generally, an amplicon or amplicons can be separated using, binding members, gel electrophoresis, chromatography or any other method capable of spatially separating the amplicons.

Figure 1:
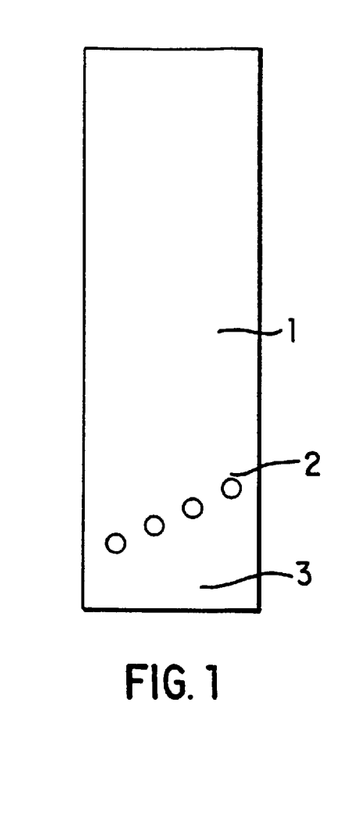
FIG. 1 illustrates an immunochromatographic strip which can be used to detect amplified nucleic acid sequences.

According to a preferred embodiment, an immunochromatographic strip is employed to spatially separate and detect multiple amplicons produced using an aggregate primer series. Such a detection configuration has previously been described in U.S. patent application Ser. No. 08/302, 646 file on Sep. 6, 1994. Generally the strip comprises a porous material suitable for transporting fluids by capillary action. At least two unique capture reagents are immobilized to the strip such that discrete spots of each capture reagent are formed at an end of the strip which is used as a contact site for a fluid which may contain the amplicons. The capture reagents are preferably spaced apart from one another in both horizontal and vertical dimensions such that a diagonal line of spots is formed. FIG. 1 shows an immunochromatographic strip configured as explained above. As shown by FIG. 1, a strip of porous material 1 is spotted with capture reagents to form a diagonal array of capture spots 2.

Capture reagents typically comprise "specific binding members" which can directly or indirectly form a specific binding pair with the amplicons. As used herein, specific binding member means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens such as adamantane and carbazole which are described in U.S. patent application Ser. No. 08/049,888 filed Apr. 21, 1993, and U.S. patent application Ser. No. 08/084,495 filed Jul. 1, 1993, respectively and antibodies specific for haptens; complementary nucleotide sequences; enzyme cofactors or substrates and enzymes; and the like. According to the embodiment being described in conjunction with FIG. 1, each capture reagent spot is typically specific for a distinct amplicon. Hence individual amplicons can be spatially separated.

After an amplification reaction, the leading edge 3 of the immunochromatographic strip, described above and shown in FIG. 1, is contacted with a reaction mixture which may contain multiple amplicons. The reaction mixture, and any amplicons contained therein, is then transported along the strip and past the capture reagent spots. If an amplicon which forms a binding pair with a binding member present at a capture site is present, it will be immobilized at a distinct capture spot on the strip. The presence of the amplicon on the strip can then be detected using a "label".

The term label refers to a molecule or moiety having a property or characteristic which is capable of detection. A label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that direct labels may require additional components such as, for example, substrates, triggering reagents, light, and the like to enable detection of the label. When indirect labels are used for detection, they are typically used in combination with a "conjugate". A conjugate is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label.

Hence, in cases where an amplicon which is immobilized to a strip carries a directly detectable label, the immobilized amplicon can be detected directly. In cases where an amplicon carries an indirect label, a conjugate comprising a binding member which is specific for the indirect label can be employed to detect the presence of the amplicon on the strip.

In general, amplicons can be detected using other techniques commonly employed to perform heterogeneous immunoassays. For example after an amplification reaction, the multiple amplicons thereby produced, if any, can be contacted with and thereby immobilized to a "solid phase reagent". Solid phase reagents may comprise a specific binding member attached or coupled to a "solid phase". Specific binding members previously mentioned can also be employed to manufacture a solid phase reagent.

Solid phase refers to any material which is insoluble, or can be made insoluble by a subsequent reaction. The solid phase can be chosen for its intrinsic ability to attract and immobilize a binding member to form a solid phase reagent. Alternatively, the solid phase can retain an additional receptor which has the ability to attract and immobilize a binding member to form a solid phase reagent. The additional receptor can include a charged substance that is oppositely charged with respect to a binding member or to a charged substance conjugated to a binding member. As yet another alternative, the receptor molecule can be any specific binding member which is immobilized upon (attached to) the solid phase and which has the ability to immobilize another binding member through a specific binding reaction. The receptor molecule enables the indirect binding of a binding member to a solid phase material before the performance of the assay or during the performance of the assay. The solid phase thus can be, for example, latex, plastic, derivatized plastic, magnetic or non-magnetic metal, glass or silicon surface or surfaces of test tubes, microtiter wells, sheets, beads, microparticles, chips, and other configurations known to those of ordinary skill in the art. It is contemplated and within the scope of the invention that the solid phase also can comprise any suitable porous material with sufficient porosity to allow, when necessary, access by a conjugate.

Microporous structures are generally preferred, but materials with gel structure in the hydrated state may be used as well. As earlier exemplified, the porous structure of nitrocellulose has excellent absorption and adsorption qualities for a wide variety of reagents including binding members. Nylon also possesses similar characteristics and also is suitable. Such materials may be used in suitable shapes, such as films, sheets, or plates, or they may be coated onto or bonded or laminated to appropriate inert carriers, such as paper, glass, plastic films, or fabrics.

There a variety of ways in which amplicons may be immobilized to a solid phase reagent. For example, the solid phase reagent may be coated with polynucleotides which form binding pairs with the amplicons. Alternatively, the amplicons may be labeled with indirect labels which form specific binding pairs with a binding member coupled to the solid phase. It will be understood that the specific binding member comprising the solid phase reagent may form binding pairs with all of the amplicons that may be produced in an amplification reaction or multiple specific binding pairs comprising the solid phase reagent may be specific for individual amplicons. Those skilled in the art will also recognize that various methods exist and may be employed to incorporate a label into an amplicon.

After amplicons, if any, are immobilized to a solid phase reagent, their presence thereon can be detected in a manner similarly to that previously explained. Specifically, labels can be employed to detect the various amplicons. In cases where the labels are not differentiated based upon a spatial separation, the labels can be differentiated in other ways such as labeling each arplicon with differentiable labels. For example, each amplicon can be labeled, directly or indirectly, with distinct fluorophores which emit light at different wavelengths. Alternatively, each amplicon could be labeled with a different enzyme each of which emits a signal in the presence of a different fluorogenic substrate. As a further alternative the amplicons can be labeled with fluorophores and enzymes and the signals can be differentiated based upon the timing at which the labels produce a signal. Specifically, the signal from a fluorophore and enzyme can be differentiated by reading a constant signal from the fluorophore and reading a rate signal from the enzyme whereby the constant signal, if any, establishes a baseline signal from which the rate signal begins. Such a detection method has been described in co-owned co-pending U.S. patent application Ser. No. 08/362,036 filed Dec. 22, 1994.

According to another embodiment, the relative quantity of a virus that may be present in a test sample can be determined using the viral genome as a target sequence. For example, an aggregate primer series for PCR can comprise three primer sets. The sensitivities of three primer sets can be determined or adjusted such that adjusted primer set 1 (APS-1) has a threshold concentration of 100 target sequences per 100 μL sample after 40 amplification cycles, adjusted primer set 2 (APS-2) has a threshold concentration of 1,000 target sequences per 100 μL sample after 40 amplification cycles, and adjusted primer set 3 (APS-3) has a threshold concentration of 10,000 target sequences per 100 μL sample after 40 amplification cycles. The sensitivities of the primers can be determined or otherwise adjusted by, for example, making a dilution series of the individual primer sets and running amplification reactions with each member of the dilution series in the presence of a selected concentration (threshold concentration) of the target sequence. Products from the various reactions can then be detected. The dilution which contains the lowest primer concentration which produces a detectable amplicon can then be employed at that concentration in the aggregate primer series.

Additionally, one member of each primer set can be labeled with a common binding member such as biotin and the remaining primer of the primer sets can be labeled with distinct labels. For example the remaining primer of APS-1 can be labeled with carbazole, the remaining primer of APS-2 can be labeled with adamantane, and the remaining primer of APS-3 can be labeled with fluorescein.

Figure 2A:
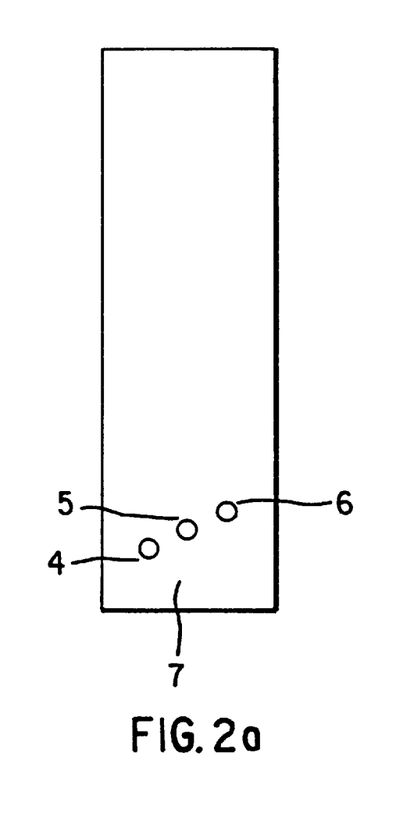
FIGS. 2a–2b illustrate a hypothetical immunochromatographic strip before and after it has been contacted with an amplification reaction mixture and the reagents necessary to detect amplified nucleic acid sequences.

A reaction mixture comprising the aggregate primer series can then be contacted with an appropriately treated 100 μl test sample which is suspected of containing the target sequence. The resulting mixture can then be cycled 40 times and an aliquot of the cycled reaction mixture can be combined with an anti-biotin conjugate comprising, for example, a binding member specific for biotin attached to selenium colloid particles. The presence of the various amplicons, if any, can then be detected. Detection can be performed with a nitrocellulose strip configured similarly to that shown in FIG. 1. However, in this case, three capture spots would be sufficient for detection. One capture spot could comprise anti-carbazole antibody, another capture spot could comprise anti-adamantane antibody and a third capture spot could comprise anti-fluorescein antibody. FIG. 2a represents such a nitrocellulose strip configuration where spot 4 is the carbazole capture spot, spot 5 is the adamantane capture spot, and spot 6 is the fluorescein capture spot. The leading edge 7 of the nitrocellulose strip can be contacted with the reaction mixture whereby the reaction mixture is transported past the capture spots. The capture spots will immobilize the various amplicons, if any, to the nitrocellulose strip at specific locations. For example, an amplicon comprising APS-1 would be immobilized at spot 4, an amplicon comprising APS-2 would be immobilized at spot 5, and an amplicon comprising APS-3 would be immobilized at spot 6.

If a sufficient quantity of amplicon were generated during amplification, enough conjugate (attached to the amplicon) would accumulate at the capture spots to produce a visible signal. A visible signal at a particular capture spot would be an indication that the adjusted primer set's threshold concentration was present in the test sample. Since the target sequence comprised the viral genome, it then follows that the virus was present at a concentration of at least that adjusted primer set's threshold concentration.

Figure 2B:
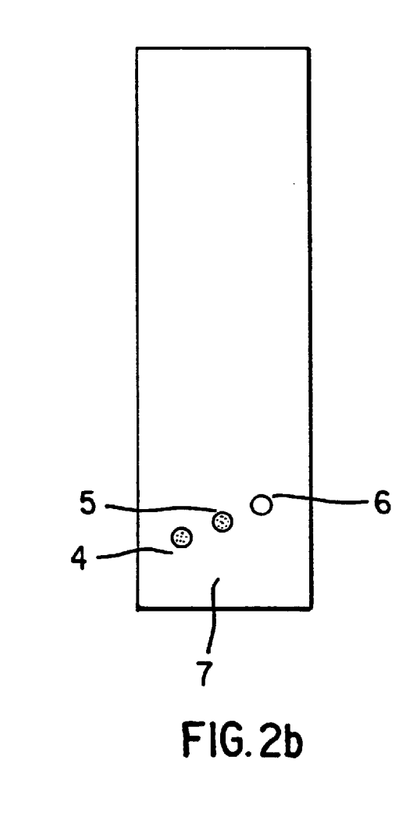

For example, assuming there were between 1,000 and 10,000 virus particles in the test sample, after the nitrocellulose strip was contacted with the reaction mixture and conjugate, it would appear as shown in FIG. 2b where the amplicon comprising APS-1 is immobilized at spot 4, and the amplicon comprising APS-2 is immobilized at spot 5. However, no signal is detected at spot 6 because APS-3's threshold concentration was not present in the test sample. Table 1 shows the results obtained from such a configuration where a positive detection of amplicon is represented with a positive sign (+) and no detectable amplicon is indicated with a negative sign (−).

TABLE 1

| | PRIMER SET | | |
|---|---|---|---|
| | APS-1 | APS-2 | APS-3 |
| Threshold Concentration | 100 copies/100μL/40 cycles | 1,000 copies/100μL/40 cycles | 10,000 copies/100μL/40 cycles |
| Detection of Amplicon | (+) | (+) | (−) |

Based on the nitrocellulose strip and the same results shown in tabular form in Table 1, it could be determined that because a positive result was obtained for APS-1 and APS-2 there was more than 100 and more than 1,000 target sequence copies in the test sample. Additionally, because APS-3 failed to yield a detectable amplicon, it could be determined that there were less than 10,000 target sequence copies in the test sample. Hence, there were between 1,000 and 10,000 target sequences in the test sample. Accordingly, there were between 1,000 and 10,000 virus particles in the test sample.

According to another embodiment, a control sequence can be employed to insure that the amplification reaction itself was efficacious. For example, two PCR primer sets APS-1 and APS-2 can be adjusted to have threshold concentrations of 1,000 target sequences per 100 µL sample after 40 amplification cycles, and 10,000 target sequences per 100 µL sample after 40 amplification cycles respectively. A known nucleic acid sequence can be used as the control sequence.

Primers for the control sequence are generally not adjusted but in some cases it may be desirable to adjust them. All that is required of the control primers is that they are capable of producing a detectable amplicon after the number of amplification cycles contemplated for the reaction in which they are to be used.

A nucleic acid amplification mixture comprising APS-1, APS-2, the control sequence, as well as the control primers is then contacted with an appropriately treated 100 µL test sample. The so-formed reaction mixture is then cycled 40 times. Detectable amplicons, if any, can then be detected in a manner similar to that previously explained. For example, the various amplicons could be associated with a directly detectable label such as a fluorophore by incorporating it into one member of each primer set. The other member of the primer sets could be labeled with distinct binding members as above. A nitrocellulose strip could be supplied with capture regions which would immobilize the control amplicon and the two primer set amplicons. After contacting such a nitrocellulose strip with an aliquot of the reaction mixture, any immobilized amplicons could then be detected by determining the presence of a fluorescent signal. As above, signals in the capture regions would indicate the presence of a particular primer set's threshold concentration. However, signal in the region employed to capture the control amplicon would indicate that amplification was effective. A lack of such a signal would indicate that amplification was not effective and therefore, the results could not be relied upon.

Assuming the target sequence was a viral genome, a positive signal in the control capture regions and no detectable signals in the remaining capture regions would indicate that (i) the amplification was effective and (ii) there were less than 1,000 viral particles in the test sample. However, if no detectable signal was obtained in either the control capture region or the adjusted primer set capture regions, it could be determined that the amplification reaction was not effective and therefore, such results could not be relied upon.

The following examples are provided to further illustrate the present invention and not intended to limit the invention.

EXAMPLES

Throughout the examples the following abbreviations have the given meanings.

BSA refers to bovine serum albumin.

EPPS refers to N-(2-hydroxyethyl) piperazine-N'-(3-propanesulfonic acid).

NAD refers to nicotinamide adenine dinucleotide.

TRIS® refers to tris-(hydroxymethyl) aminomethane.

TTP refers to thymidine triphosphate.

Example 1

Probe Set Concentration Adjustment and Simultaneous LCR Amplification of β-Globin & HIV Minor Target Sequences In this example, a process for adjusting or determining a primer set's threshold concentration is demonstrated. Two minor target sequences at widely differing concentrations were co-amplified using LCR, and the effects of varying the concentration of a primer set on that primer set's sensitivity is presented.

One minor target sequence (SEQ ID No. 1) is presented as a single strand for simplicity but was actually used in duplex form. SEQ. ID. No. 1 corresponds to map positions 62252 to 62288 of the Human β-Globin gene as disclosed in GenBank, Accession No. J00179, NCBI SEQ. ID. No.: 183807. The other minor target sequence (SEQ. ID. No. 2), which is also presented as a single strand for simplicity, was also employed in its duplexed form. SEQ. ID. No. 2 corresponds to map positions 3554 to 3601 of the HIV pol gene as disclosed in Sanchez-Pescador R., et.al., *Science* 277: 484–492 (1985). Both sequences are shown below in Table 2 in a 5' to 3' direction.

TABLE 2

| SEQ. ID No | 5'-Sequence-3' |
|---|---|
| 1 | GGGCAAGGTGAACGTGGATGAAGTTGGTGGTGAGGCC |
| 2 | GGCAAGGCCAATGGACATATCAAATTTATCAAGAGCCATTTAAAAATC |

Target-specific probes (also referred to herein as "amplification probes") were designed to amplify and detect the above target sequences by LCR. The first amplification probe set was specific for SEQ. ID. No. 1 (the "β-Globin sequence") and its complementary strand. Two probes (SEQ. ID. No. 3 and SEQ. ID. No. 4) from this set were haptenated with biotin which is designated "Bt". One of the remaining probes (SEQ.ID No. 6) was haptenated with adamantane which is designated "Ad". The 5' ends of SEQ. ID. No. 4 and SEQ. ID. No. 5 were functional with a phosphate group, which is designated "P", to allow ligation of SEQ. ID. No. 3 to SEQ. ID. No. 5 and ligation of SEQ. No. 4 to SEQ. ID. No. 6. SEQ. ID. No. 4 and SEQ. ID. No. 6 were complementary to SEQ. ID. No. 1, and SEQ. ID. No. 3 and SEQ. ID. No. 5 were complementary to SEQ. ID. No. 1's complementary strand. The probe set employed to amplify and detect the β-Globin sequence is shown below in Table 3 where individual probes are listed in a 5' to 3' direction.

TABLE 3

| SEQ. ID. No. | 5'-Sequence-3' |
|---|---|
| 3 | BtGGGCAAGGTGAACGTGGA |
| 4 | pCCACGTTCACCTTGCCCBt |
| 5 | pGAAGTTGGTGGTGAGGCC |
| 6 | AdGGCCTCACCACCAACTTCA |

The other amplification probe set was designed to amplify and detect SEQ. ID. No. 2 (the "HIV sequence) and its complementary strand. Two of the probes (SEQ. ID. No. 7 and SEQ. ID. No. 8) were haptenated with fluorescein, designated "Fl", and the other two probes (SEQ. ID. No. 9 and SEQ. ID. No. 10) were haptenated with biotin. SEQ. ID. No. 8 and SEQ. ID. No. 10 hybridize with SEQ. ID. No. 2, and SEQ. ID. No. 7 and SEQ. ID. No. 9 hybridize with SEQ. ID. No. 2's complementary strand. As above, "p" designates a phosphate group. The probe set employed to amplify and detect the HIV sequence is shown below in Table 4 where individual probes are listed in a 5' to 3' direction.

TABLE 4

| SEQ. ID. No. | 5'-Sequence-3' |
|---|---|
| 7 | FlGGCAAGGCCAATGGACATATCAAA |
| 8 | pGATATGTCCATTGGCCTTGCCFl |
| 9 | pATCAAGAGCCATTTAAAAATCBt |
| 10 | BtGATTTTTAAATGGCTCTTGATAAA |

The probe sets described above were used at various concentrations to co-amplify the minor target sequences according to GLCR essentially as described in EP-A-439 182. The reaction components for performing each reaction were: 50 mM EPPS buffer, pH 7.8; 20 mM K$^+$; 30 mM MgCl$_2$; 10 $\mu$M NAD; 1.7 $\mu$M TTP; 90 U/$\mu$L ligase (Molecular Biology Resources; Milwaukee, Wis.), 0.01 U/$\mu$L Taq polymerase (Perkin-Elmer; Norwalk, Conn.) and probes in concentrations shown in Table 5 below. Each reaction had 100 $\mu$L final volume. The above components were made at a 2x concentration and aliquotted to capillary tubes. The target sequences (as shown in table 5) were also at 2x concentration but were heated at 100° C. for 3 minutes and then cooled before adding to the capillary tubes.

Thermal cycling was performed in a capillary thermal cycler which is described in U.S. patent application Ser. No. 08/140,731, filed Oct. 21, 1993. Fifty of the following cycles were performed using the capillary thermal cycler: 88° C. for 10 seconds and 53° C. for 60 seconds.

The probe set concentrations and the amount of their respective minor target sequences per reaction are shown below in Table 5.

TABLE 5

| Reaction Number | HIV subTarget (molecules) | HIV Probe Set (molecules) | β-Globin subTarget (molecules) | β-Globin Probe Set (molecules) |
|---|---|---|---|---|
| 1 | 0 | 1 × 10$^{12}$ | 0 | 5 × 10$^{10}$ |
| 2 | 0 | 1 × 10$^{12}$ | 1 × 10$^5$ | 5 × 10$^{10}$ |
| 3 | 10 | 1 × 10$^{12}$ | 1 × 10$^5$ | 5 × 10$^{10}$ |
| 4 | 100 | 1 × 10$^{12}$ | 1 × 10$^5$ | 5 × 10$^{10}$ |
| 5 | 0 | 0 | 1 × 10$^5$ | 5 × 10$^{10}$ |
| 6 | 0 | 0 | 0 | 5 × 10$^{10}$ |
| 7 | 0 | 1 × 10$^{12}$ | 0 | 7.5 × 10$^{10}$ |
| 8 | 0 | 1 × 10$^{12}$ | 1 × 10$^5$ | 7.5 × 10$^{10}$ |
| 9 | 10 | 1 × 10$^{12}$ | 1 × 10$^5$ | 7.5 × 10$^{10}$ |
| 10 | 100 | 1 × 10$^{12}$ | 1 × 10$^5$ | 7.5 × 10$^{10}$ |
| 11 | 0 | 0 | 1 × 10$^5$ | 7.5 × 10$^{10}$ |
| 12 | 0 | 0 | 0 | 7.5 × 10$^{10}$ |

GLCR amplification products were detected using an immunochromatographic strip which was configured as follows: 7 mm×40 mm strips of nitrocellulose (available from Schleicher & Schuell; Keene, NH) were jetted with 4 antibody spots (anti-adamantane, anti-quinoline, anti-dansyl and anti-fluorescein) from bottom left to upper right to form a diagonal array of capture spots. Each capture spot was jetted with 6.49×10$^{-10}$ $\mu$L of the antibody solutions. The anti-quinoline, anti-dansyl and anti-fluorescein antibodies were at a 0.5 mg/mL concentration; and the anti-adamantane antibody was at a 1.0 mg/mL concentration. All antibody solutions were made with TBS (TRIS® buffered saline) with 0.1% BSA and a grain of phenol red.

After amplification, a 5 $\mu$L sample of the reaction product was added to 25 $\mu$L of a blue latex conjugate at 0.05% solids, and 20 $\mu$L of 3% casein in TBS. The blue latex conjugate was made by vortexing blue latex microparticles (0.4% solids available from Bangs Laboratories; Carmel, Ind.) with a 10 $\mu$g/ml solution of rabbit antibiotin antibody for 30 seconds. The conjugate was blocked with 0.05% casein in 10 mM TRIS® buffer. The conjugate/reaction sample solution was mixed and the biotin haptenated ends of the amplicons were thereby complexed with the anti-biotin blue latex conjugate.

The solution was then contacted with the immunochromatoraphic strip as configured above. The solution migrated up the strip and the antibody spots captured any specific haptens. Amplicons produced during tye amplification reaction were captured on the immunochromatographic strip which resulted in the concentration of blue latex at appropriate cature spots.

As expected and as evidenced by all of the strips (data not shown), no signal was observed at the quinoline and dansyl capture spots. However, varying amounts of signal were observed at the fluorescein and adamantane capture spots. The signal intensity at these spots increased with an increase in probe concentration. Hence, the sensitivity of the probe set increased with an increase in its concentration in the amplification reaction. Thus, by varying the concentration of the probe set its sensitivity can be controlled. Additionally, although the probes were directed against different targets, the threshold concentrations for the probe sets were different (the β-globin set is recognizing 1×10$^5$ targets at a similar signal intensity as the HIV set which is recognized 10–100 copies of HIV).

Example 2

Primer Set Concentration Adjustment and Simultaneous PCR Amplification of Two Hepatitis B Virus (HBV) Target Sequences In this example, simultaneous PCR of two separate sub-target regions of an HBV target sequence is performed using two primer sets which have widely differing sensitivities.

The first sub-target sequence corresponds to map positions 236 to 712 of HBV as disclosed in Ono Y., et al., *Nucleic Acids Res.*, 11:(6), 1747–1757, (1983) and Okamoto H., et al., *J. Gen. Virol.*, 69: 2575–2583 (1988). The entire sequence is listed below in Table 7 as SEQ. ID. No. 11 in a single stranded format for simplicity of explanation. This sequence will be referred to hereinafter as the "long HBV target". The other sub-target sequence employed in this example corresponds to map positions 1863 to 1934 of HBV as disclosed in Okamoto H., et al., *J. Gen. Virol.*, 69: 2575–2583 (1988). This sequence (SEQ. ID. No. 12) is similarly listed below in Table 7 as a single stranded sequence and will be referred to hereinafter as the "short HBV target". Both sub-targets are listed in Table 7 in the 5' to 3' direction.

TABLE 7

| SEQ ID. No. | 5'-sequence-3' |
|---|---|
| 11 | ATACCACAGAGTCTAGACTCGTGGTGGACTTCTCTCAATTTTCTAGGGGGAACAC CCGTGTGTCTTGGCCAAAATTCGCAGTCCCAAATCTCCAGTCACTCACCAACCTG TTGTCCTCCAATTTGTCCTGGTTATCGCTGGATGTGTCTGCGGCGTTTTATCATC TTCCTCTGCATCCTGCTGCTATGCCTCATCTTCTTGTTGGTTCTTCTGGACTATC AAGGTATGTTGCCCGTTTGTCCTCTAATTCCAGGATCATCAACAACCAGCACCGG ACCATGCAAAACCTGCACAACTCCTGCTCAAGGAACCTCTATGTTTCCCTCATGT TGCTGTACAAAACCTACGGATGGAAACTGCACCTGTATTCCCATCCCATCATCTT GGGCTTTCGCAAAATACCTATGGGAGTGGGCCTCAGTCCGTTTCTCTTGGCTCAG TTTACTAGTGCCATTTGTTCAGTGGTTCGTAGGGCTT |
| 12 | TTCAAGCCTCCAAGCTGTGCCTTGGGTGGCTTTGGGGCATGGACATTGACCCGTA TAAAGAATTTGGAGCTT |

The PCR probes employed to amplify and detect the above sub-target sequences are listed below in Table 8. SEQ. ID. No. 13 matches part of the long HBV sequence listed above and hybridizes to its complementary strand. SEQ. ID. No. 14 hybridizes to the long HBV sequence listed above. Collectively, SEQ. ID. No. 13 and SEQ. ID. No. 14 will hereinafter be referred to as the "long sequence probes". SEQ. ID. No. 15 matches part of the short HBV sequence listed above and hybridizes to its complementary strand. SEQ. ID. No. 16 hybridizes to the short HBV target sequence listed above. Collectively, SEQ. ID. No. 15 and SEQ. ID. No. 16 will hereinafter be referred to as the "short sequence probes". After PCR, the long sequence probes yield, approximately, a 477 base product and the short sequence probes yield, approximately, a 72 base product. All of these probes are listed below and are in the 5' to 3' direction. Accordingly, SEQ. ID. No. 13 and SEQ. ID. No. 15 are in the forward direction, and SEQ. ID. No. 14 and SEQ. ID. No. 16 are in the reverse direction.

TABLE 8

| SEQ. ID. No. | 5'-sequence-3' |
|---|---|
| 13 | ATACCACAGAGTCTAGACTCGTGGTGGACT |
| 14 | AAGCCCTACGAACCACTGAACAAATGGCAC |
| 15 | TTCAAGCCTCCAAGCTGTGCCTTGG |
| 16 | AAGCTCCAAATTCTTTATACGGGTCAATG |

The probes listed above in Table 8 were used in PCR essentially as described in U.S. Pat. No. 4,683,195 and U.S. Pat. No. 4,683,202. PCR was performed in 0.65 mL Gene-Amp thin-walled reaction tubes (from Perkin-Elmer; Norwalk, Conn.) in 25 μl volumes containing the following components: 1× PCR buffer (10 mM TRIS®-HCL, pH 8.3, 40 mM KCl, 0.001% w/v gelatin), 3 mM MgCl$_2$, 200 μM of each dNTP, 2.5 U Amplitaq™ (all from Perkin-Elmer; Norwalk, Conn.), 0.55 μg TaqStart™ Antibody (Clontech; Palo Alto, Calif.), primers at 200 nM for the long sequence probes, and 1 μM for the short sequence probes. Each tube had one drop of mineral oil.

PCR for both sub-target sequences was run in duplicate and the sub-target sequences were added to the Gene-Amp tubes in the form of HBV genomic DNA purified from the Abbott HBV Assay positive control (available from Abbott Laboratories, Abbott Park, Ill.). Accordingly, the HBV genome was used as a target sequence. The amount of target sequence added to each duplicate tube varied and is set forth below. After all reagents and targets were placed in the tubes, they were heated to 94° C. for 2 minutes. The mixtures were then subjected to 40 cycles of programmed temperature change, the cycle being 94° C. for 30 seconds, 67° C. for 1 minute. After cycling, the tubes were stored at 4° C. The thermal cycling was performed in a PE480 thermal cycler available from Perkin-Elmer, Norwalk, Conn.

After cycling, 10 μL aliquots from the tubes were removed, mixed with 3 μL of a bromophenol blue, xylene cyanol, phenanthridinium triamine (PTA—disclosed in U.S. patent application Ser. No. 08/265,342, filed Jun. 23, 1994) and glycerol (final concentration in the mixture was 7.7 μM PTA, 7.7% glycerol, trace amounts of bromophenol blue and xylene cyanol). The resulting mixtures were run on a precast Bio-Rad Ready Gel (10% acrylamide) (BioRad; Hercules, Calif.) (100 V, bromophenol blue run to the bottom of the gel). The gel was photographed and is shown in FIG. 3.

Figure 3:
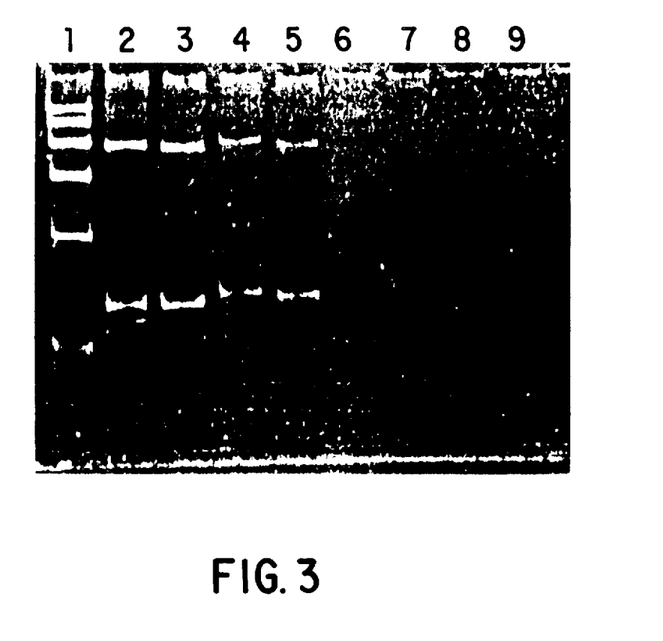
FIGS. 3 and 4 are photographic representations of gels used to detect the products of amplification reactions using a pair of PCR primer sets to amplify two distinct target sequences which were contained in a single reaction vessel. The concentrations of the primer sets and target sequences are explained more fully in Example 2 below.

Molecular weight markers were run in the first lane of the gel shown in FIG. 3. The markers comprised Promega PCR Markers 45694 (available from Promega; Madison, Wis.) having the following lengths 1000 bp, 750 bp, 500 bp, 300 bp, 150 bp, 50 bp. PCR products produced from various target sequence concentrations were run in the remaining lanes of the gel. Duplicate tubes were run for the various concentrations of the target sequence. Lanes 2 and 3 were samples from tubes where PCR co-amplification was run on approximately 30,000 HBV DNA molecules. Lanes 4 and 5 were samples from tubes where PCR co-amplification was run on approximately 300 molecules of HBV DNA. Lanes 6 and 7 were samples from tubes where PCR co-amplification was run on approximately 30 molecule of HBV DNA. Lanes 8 and 9 were samples from control tubes where PCR co-amplification was run without any HBV DNA.

As shown by the gel the sensitivities of the two sets are nearly equivalent at the different concentrations. Specifically, at 30,000 and 300 major target sequences, both probe sets produced detectable amplicons after PCR. However, the two probe sets did not produce detectable amplicons when less than 300 target sequences were contained in the sample.

The sensitivities of the probe sets were then adjusted by varying the concentration of one of the probe sets employed in PCR. In this round of amplification all the reagents and cycling conditions were the same as above with the exception of the concentration of the long probe set which was 60 μM.

Figure 4:
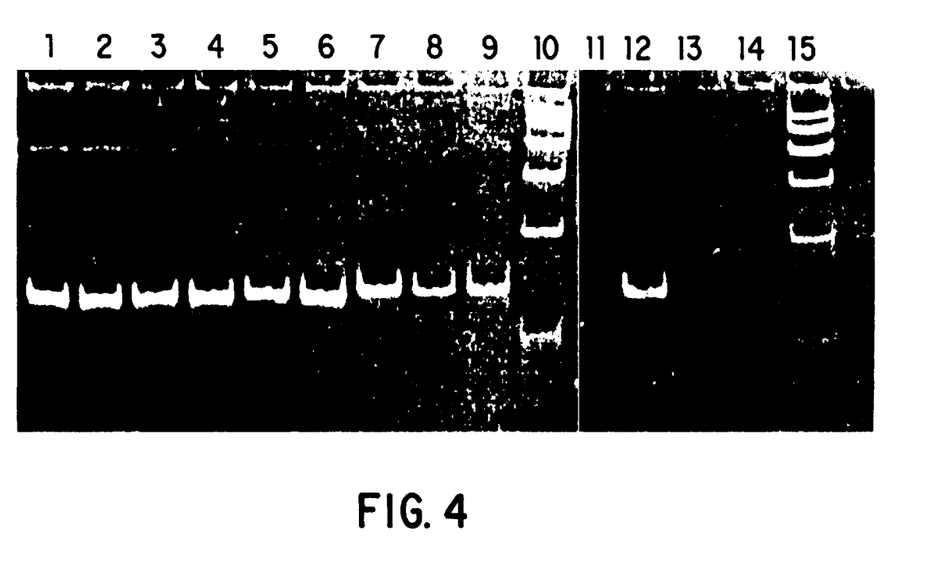

The tubes were cycled as above, sampled as above and run on a gel as above. The resulting gel was photographed and a representation of the photograph is shown in FIG. 4. Table 9 gives the lane numbers of replicate tubes and the amount of HBV DNA placed in the tubes prior to amplification. Lane 11 was a blank lane and lanes 10 and 15 contained the molecular weight markers previously set forth.

TABLE 9

| Lanes | HBV DNA (molecules approx.) |
| --- | --- |
| 1 and 2 | $3 \times 10^6$ |
| 3 and 4 | $3 \times 10^5$ |
| 5 and 6 | $3 \times 10^4$ |
| 7 and 12 | 3000 |
| 8 and 9 | 300 |
| 13 and 14 | no target |

As evidenced by the gel shown in FIG. 4, adjusting the long probe set by decreasing its concentration caused its sensitivity to decrease. At the probe set concentrations used, the long probe set did not produce a detectable amplicon until the HBV concentration was at $3 \times 10^5$ molecules. Hence, under the above conditions, the long probe set's threshold concentration was $3 \times 10^5$. On the other hand, the long probe set's threshold concentration was less than 300 HBV molecules. Using the probe sets under the above conditions and at the above concentrations, the relative amount of an unknown amount of HBV in a test sample could be determined. Specifically, it could be determined if at least 300, between 300 and $3 \times 10^5$ or more than $3 \times 10^5$ HBV DNA genome molecules were present in a test sample. This could then be correlated to the amount of HBV in a test sample.

While the invention has been described in detail and with reference to specific embodiments, it will be apparent to one skilled in the art that various changes and modifications may be made to such embodiments without departing from the spirit and scope of the invention. Additionally, all patents and publications mentioned above are herein incorporated by reference.

What is claimed is:

1. A method for determining an approximate amount of a target nucleic acid sequence in a test sample comprising the steps of:

(a) contacting said test sample with a nucleic acid amplification reaction mixture comprising a first primer set capable of hybridizing with a first sub-target region of said target nucleic acid sequence, and a second primer set capable of hybridizing with a second sub-target region of said target nucleic acid sequence, wherein said first and said second sub-target regions are different and wherein said first and said second primer sets are selected such that
  (i) said first primer set is capable of producing a detectable amplicon at or above a first pre-selected threshold concentration of said target nucleic acid sequence,
  (ii) said second primer set is capable of producing a detectable amplicon at or above a second pre-selected threshold concentration of said target nucleic acid sequence, and
  (iii) said first and second threshold concentrations are different from one another;

(b) subjecting the reaction mixture to amplification conditions sufficient to produce a detectable amplicon from said primer sets when said test sample contains a concentration of target nucleic acid sequence which is at or above the different threshold concentrations at which the primer sets are capable of producing a detectable amplicon; and (c) detecting whether amplicons are produced in said reaction mixture from said primer sets so as to determine whether the test sample contains a concentration of target nucleic acid sequence at or above said threshold concentrations corresponding to said primer sets.

2. The method of claim 1 wherein said amplification conditions comprise thermal cycling said reaction mixture between 20 and 100 times.

3. The method of claim 1 wherein said primer sets are LCR probe sets or PCR primer sets.

4. The method of claim 1 wherein at least one member of each of said primer sets includes a label.

5. The method of claim 4 wherein detecting whether amplicons are produced comprises the steps of:

(a) contacting said reaction mixture with a solid phase reagent to form amplicon/solid phase reagent complexes;

(b) contacting said amplicon/solid phase reagent complexes with a conjugate; and (c) detecting a signal as an indication of the presence of said amplicons.

6. The method of claim 4 wherein said label is directly detectable.

7. The method of claim 6 wherein detecting whether amplicons are produced comprises the steps of:

(a) contacting said reaction mixture with a solid phase reagent to form amplicon/solid phase reagent complexes; and (b) detecting a signal as an indication of the presence of said amplicons.

8. The method of claim 7 wherein said solid phase reagent comprises a nitrocellulose strip coated with binding members.

9. The method of claim 8 wherein said binding member is an oligonucleotide or an antibody.

10. The method of claim 1 wherein at least one primer set's sensitivity is adjusted.

11. The method of claim 10 wherein said sensitivity is adjusted by concentration adjustment.

12. The method of claim 1 wherein said amplification reaction mixture further comprises a third primer set capable of hybridizing with a third sub-target region of said target nucleic acid sequence, wherein said third sub-target region is different than said first and said second sub-target regions and wherein said third primer set is selected such that (a) said third primer set is capable of producing a detectable amplicon essentially only at or above a third threshold concentration of said target nucleic acid sequence; and (b) said third threshold concentration is different from said first and second threshold concentrations.

13. The method of claim 1 wherein said target nucleic acid sequence is a viral genome or a bacterial genome.

* * * * *